United States Patent [19]

Dunn

[11] Patent Number: 5,486,506
[45] Date of Patent: Jan. 23, 1996

[54] METHOD FOR TREATING CARDIAC INOTROPIC IRREGULARITIES

[75] Inventor: Michael Dunn, New Rochelle, N.Y.

[73] Assignee: Meditech, Ltd., Chappaqua, N.Y.

[21] Appl. No.: 281,767

[22] Filed: Jul. 28, 1994

Related U.S. Application Data

[63] Continuation of Ser. No. 934,178, Aug. 21, 1992, abandoned.

[51] Int. Cl.$^6$ ................. A61K 31/19; A61K 31/705; A01N 37/00
[52] U.S. Cl. ................. 514/26; 514/557; 514/821; 536/5; 554/224
[58] Field of Search ................. 514/26, 560, 821, 514/557, 821; 536/5, 6, 61; 554/224

[56] References Cited

U.S. PATENT DOCUMENTS

| | | | |
|---|---|---|---|
| 4,906,467 | 3/1990 | Schwartzman et al. | 514/560 |
| 5,102,670 | 4/1992 | Abraham | 424/650 |

OTHER PUBLICATIONS

Otsuji et al. *Igaku no Ayumi*, 151(9), pp. 563–564, (1989) [Abstract only].

Kuzuya et al. *Cardiovascular Res.*, 21(8), pp. 551–558, (1987) [Abstract only].

McCluskey et al. *Prostaglandins*, 29(3), pp. 387–403, (Mar. 1985) [Abstract only].

Masferrer et al., Invest. Opthalmol. Visual Sci. 31(3):535–536 (Mar. 1990).

Masferrer, Biochem. Pharmacology, 39(12):1971–1974 (1990).

Geroski et al., Invest. Opthalmol. Visual Sci., 31 (No. 716[(p. 145(1990).

Edelhauser, Invest. Opthalmol. Visual Sci. 32(4) No. 2491, p. 1177 (1991).

*The Merck Index*, 10th Ed.; Windholz et al, Eds. (1983) pp. 458–459, 676, 990.

Goodman & Gilman's, The Pharmacological Basis of Therapeutics 7th Ed. (1985) pp. 718–738.

*Primary Examiner*—Douglas W. Robinson
*Assistant Examiner*—Howard C. Lee
*Attorney, Agent, or Firm*—Felfe & Lynch

[57] ABSTRACT

The invention describes a method for normalizing a cardiac inotropic irregularity, via administering an effective amount of 12(R)HETE. Also described are therapeutic compositions which combine a cardiac glycoside and 12(R)HETE.

12 Claims, 1 Drawing Sheet

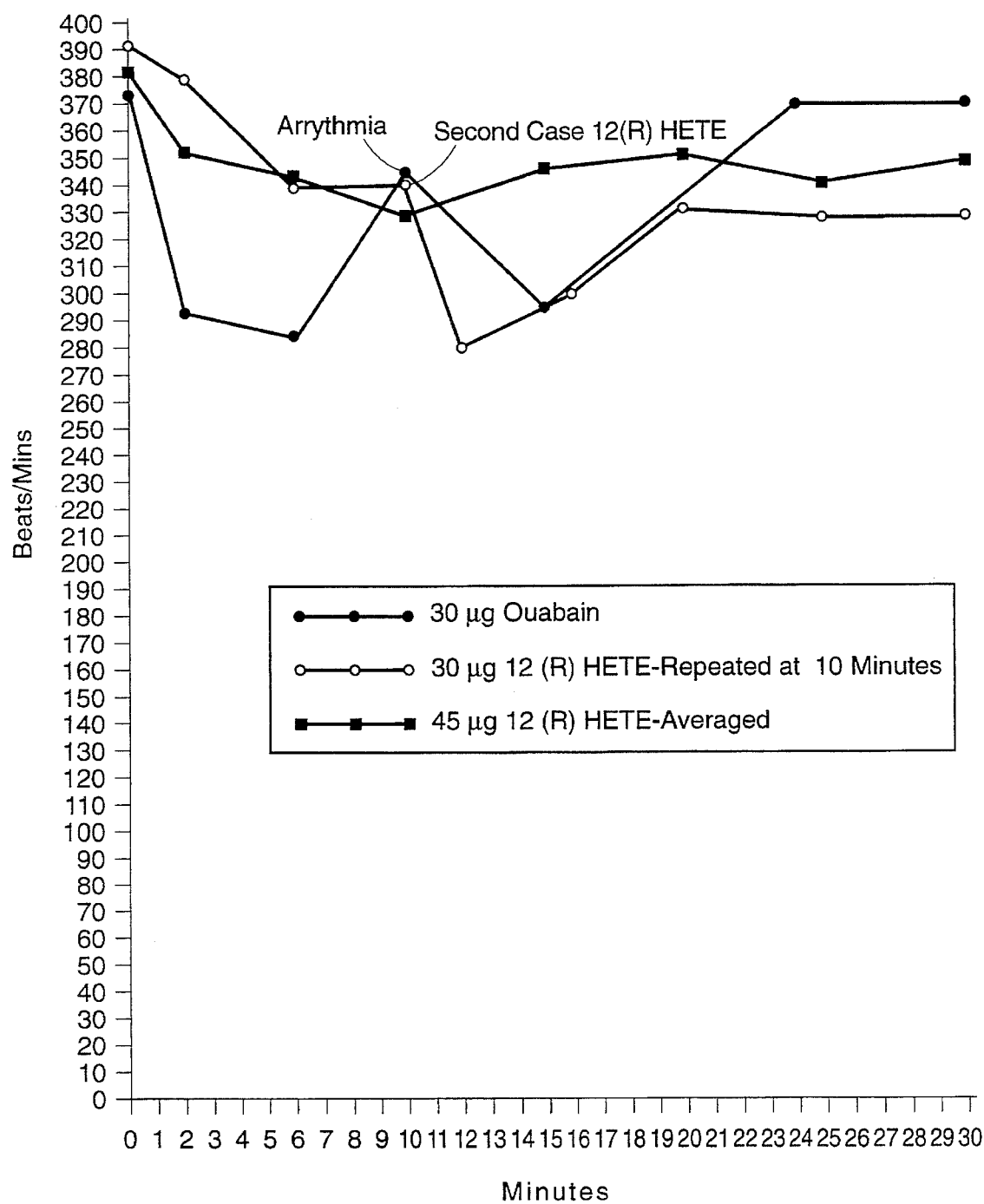

METHOD FOR TREATING CARDIAC INOTROPIC IRREGULARITIES

This application is a continuation of application Ser. No. 07/934,178, filed Aug. 21, 1992, now abandoned.

FIELD OF THE INVENTION

This invention relates to the treatment of cardiac disorders characterized by inotropic irregularities. More particularly, it relates to the treatment of these disorders via administration of the compound referred to as "12(R)HETE", or 12(R)-hydroxyeicosateraenoic acid". For convenience, the acronym will be used hereafter.

BACKGROUND OF THE INVENTION

The compound referred to as 12(R)HETE was described as $Na^+$-$K^+$ ATPase inhibitor by Masferrer et al., Inv. Opthal & Vis. Sci 31(3): 535–539 (1990). This reference showed that the referenced compound caused normal intraocular pressure to drop when administered to the eyes of the rabbits. The compound was implicated in control of ATPase levels, as may be seen in, e.g., U.S. Pat. No. 5,102,670 to Abraham et al., the disclosure of which is incorporated by reference. The reference discloses how 12(R)HETE inhibits ocular ATPase, leading to an increase in ocular swelling. The patent presents a method for preventing ocular swelling by inhibiting hemeoxygenase production, as this enzyme leads to increased production of the 12(R)-HETE compound.

Masferrer et al., Biochem. Pharmacol. 39(12): 1971–74 (1990) describe experiments in which partially purified enzyme compositions were tested in combination with 12(R)HETE. In vitro experiments were carried out using renal, cardiac and corneal forms of $Na^+K^+$ dependent ATPase. The authors comment, at page 1974 that "(T)he effectiveness of 12(R)HETE in in vitro situations remains uncertain." The paper also describe experiments where 12(R)HETE, ouabain, and combinations of the two drugs were used on corneal and renal enzymes. Table 4 of this paper shows a minimal effect of 12(R)HETE when combined with ouabain, suggesting that whatever mechanism is involved, it is the same for ouabain and 12(R)HETE.

Ouabain is a member of the class of compounds known as the cardiac glycosides. The most well known member of this family of compounds is probably digitalis. These compounds are used in cardiac therapy because of their shared effects on the heart. Specifically, they are implicated in the inhibition of $Na^+$, $K^+$ dependent ATPase, and enable more forceful and efficient heart contraction. A problem with therapies involving the regulation of cardiac disorders with the glycosides, however, is that they lead to cardiac arrythmias and conductive defects. If one assumes—as current theory does—that the glycosides lead to increases in intracellular $Na^+$ levels, this must cause a drop in $K^+$ levels in order to maintain isosmotic status. Concentrations of $K^+$ in the $Na^+$-$K^+$ relationship are smaller, however, and when the $K^+_{[intercellular]}/K^+_{[intracellular]}$ ratio changes, intracellular potential is brought to the point where diastolic depolarization— and glycoside induced arrythmias and conductive defects—can and do occur.

Thus, current therapy for heart disorders characterized by inotropic irregularities is faced with a dilemma. While the drugs of choice to appear to inhibit the implicated $Na^+$, $K^+$ dependent ATPase, the risk of cardiac arrythmia and conductive defects is great. Useful therapies are sought where the inotropic irregularities can be treated without the risk of cardiac arrythmia and conductive defects.

It has now been found, surprisingly, that the compound 12(R)HETE can be used in vivo to regulate cardiac inotropic irregularities, without the risk of arrythmia. This result is surprising in view of the shared ability of 12(R)HETE and the cardiac glycosides to regulate $Na^+K^+$ dependent ATPase, previously thought to be secured via the same mechanism.

The invention will be explained in further detail by the examples which follow.

BRIEF DESCRIPTION OF THE FIGURE

FIG. 1 compares the in vivo efficacy of 12(R)HETE and the representative cardiac glycoside ouabain.

DETAILED DESCRIPTION OF PREFERRED EMBODIMENTS

EXAMPLE 1

An in vitro study was carried out to compare the effect of ouabain and 12(R)HETE on the heart.

Subject animals (frogs), were killed, and intact hearts were removed immediately thereafter. Each organ was placed in a separate petri dish with 30 ml of physiologically balanced saline solution with added calcium, at room temperature. No contractions were observed at this point.

The hearts then were administered 10 ul of either of 0.25 umol ouabain, or of 12(R)HETE (50 ug in 60 ul PBS). In each case, contractions immediately resulted.

The agents were administered at the same dose at 4, 6, and 9 minutes. Over this period, all hearts continued to beat. The 12(R)HETE treated hearts ceased contraction after 10 minutes; however, an additional 10 ul dose of the 12(R)HETE caused contractions to return for another 18 minutes.

The ouabain treated hearts continued to contract, but stopped after 15 minutes. Additional doses failed to elicit renewed contractions. When these hearts were transferred to the ouabain containing petri dishes, however, contractions immediately returned, and continued for another 21 minutes.

EXAMPLE 2

A comparison between ouabain and 12(R)HETE was carried out in rabbits.

Identical amounts (30 mg) of ouabain and 12(R)HETE were dissolved in 1 cc of physiological saline. The formulations were each administered intravenously to normal, New Zealand albino rabbits.

The rabbit which received the ouabain showed a prompt reduction in heart rate, and a cardiac arrythmia developed after 10 minutes. The arrythmia lasted for 10 minutes thereafter.

The 12(R)HETE showed a more modest rate lowering effect upon administration, but no arrythmia was observed. These results are shown in FIG. 1. When a repeat, 30 mg dose of 12(R)HETE was administered, heart rate was reduced to slightly less than that obtained with ouabain, and the effect was somewhat prolonged.

EXAMPLE 3

Another test of 12(R)HETE's effect was carried out, using a dose of 45 mg in 1 cc of physiological saline. Two rabbits received this dosage, and the effect is also shown in FIG. 1. A drop in heart rate was observed, but it was somewhat more modest, and arrythmia was not observed.

The foregoing examples demonstrate that 12(R)HETE shares the ability to inhibit $Na^+K^+$ dependent ATPase with cardiac glycosides, but does not induce arrythmia. The first example shows that the molecule will provoke contraction even when the heart is in extremis, a property previously recognized for digitalis, ouabain, and the other cardiac glycosides. This is due to the ability to inhibit the aforementioned enzyme.

The experiments described in examples 2 and 3 show that ouabain does in fact lead to arrythmia along with the effect on heart contraction. In contrast, the 12(R)HETE of the invention does not put the subject at risk of arrythmia, or at least reduces the level of risk to the recipient.

Example 1 also suggests that, in vivo, 12(R)HETE functions via a mechanism differing from the cardiac glycosides with respect to enzymatic inhibition. It is noted that while the glycoside was no longer effective, hearts previously treated with the glycoside were caused to continue contraction after contacted with 12(R)HETE. At present, however, the suggestion of a different mechanism remains just that, and the inventors do not wish to be limited to this single possible explanation of the manner in which the compound functions. There is evidence for a different mechanism, as Holley et al., Inv. Opthal. & Vis. Sci. 33(4): 924 (1992) show that ouabain and 12(R)Hete effected ATPase differently when applied to corneal epithelial cells. Differences in corneal swelling and at the ultrastructural level were observed.

The foregoing examples thus suggest a method for regulating cardiac inotropic irregularities via administration of an amount of 12(R)HETE to a subject sufficient to normalize the irregularity, Examples of conditions which can be so treated are congestive heart failure, atrial fibrillation, atrial flutter and supraventricular tachycardia. Other conditions which can be treated by administration of 12(R)HETE will be clear to the skilled artisan, who is presumably familiar with inotropic irregularities as these apply to cardiac conditions.

The 12(R)HETE may be administered in any of the usual therapeutic modes, including, but not being limited to intravenous, sublingual, and oral administration. The compound may be administered in the form of a solution, such as a parenteral solution, an intravenous drip, and so forth, or in the form of a tablet, dragree, syrup, chewing gum, or any of the other formulations commonly known to the art.

The amount of 12(R)HETE necessary for efficacy will vary, depending on many factors including the subject, the condition being treated, the severity of the condition, and the manner in which the drug is administered. Generally, a dosage of from about 2.5 to about 4.0 mg/kg of body weight when using an intravenous solution, or from about 6.0 mg/kg of body weight if administered orally. These ranges should only be considered generally guidelines, however, in view of the degree of variability possible in subjects.

The examples also suggest another feature of the invention, which is a therapeutic composition containing an effective amount of a cardiac glycoside, such as ouabain or digitalis in combination with 12(R)HETE. Such compositions may be in any of the forms described supra, and contain a sufficient amount of the inotropic regulating medicaments to be effective.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. A method for treating a subject with a cardiac disorder associated with an inotropic irregularity, wherein said inotropic irregularity is selected from the group consisting of atrial fibrillation, heart flutter and supraventricular tachycardia comprising administering to said subject an amount of 12(R) hydroxyeicosatetraenoic acid (12(R)HETE)sufficient to regulate said inotropic irregularity without inducing arrythmia in said subject.

2. The method of claim 1, wherein said inotropic irregularity is atrial fibrillation.

3. The method of claim 1, wherein said inotropic irregularity is heart flutter.

4. The method of claim 1, wherein said inotropic irregularity is supraventricular tachycardia.

5. The method claim 1, wherein said 12(R)HETE is administered intravenously.

6. The method of claim 1, wherein said 12(R)HETE is administered sublingually.

7. The method of claim 1, wherein said 12 (R)HETE is administered orally.

8. The method of claim 1, wherein said 12(R)HETE is administered in the form of a solution.

9. The method of claim 1, wherein said 12(R)HETE is administered in the form of a tablet.

10. The method of claim 1, wherein said 12(R)HETE is administered in an amount ranging from about 2 mg to about 6 mg per kg of body weight.

11. The method of claim 6, wherein said 12(R)HETE is administered in an amount ranging from 2.5 mg to about 4 mg per kg of body weight.

12. The method of claim 8, wherein said 12(R)HETE is administered in an amount ranging from about 2 mg to about 6 mg per kg of body weight.

* * * * *